US010967055B2

(12) United States Patent
Samuel et al.

(10) Patent No.: US 10,967,055 B2
(45) Date of Patent: Apr. 6, 2021

(54) VACCINE FOR IMMUNIZATION AGAINST Q-FEVER

(71) Applicant: The Texas A&M University System, College Station, TX (US)

(72) Inventors: James E. Samuel, College Station, TX (US); Erin J. Van Schaik, Bryan, TX (US); Anthony E. Gregory, Bryan, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 16/113,924

(22) Filed: Aug. 27, 2018

(65) Prior Publication Data

US 2019/0083598 A1 Mar. 21, 2019

Related U.S. Application Data

(60) Provisional application No. 62/550,625, filed on Aug. 27, 2017.

(51) Int. Cl.
| A61K 39/00 | (2006.01) |
| A61K 39/02 | (2006.01) |
| A61K 39/39 | (2006.01) |

(52) U.S. Cl.
CPC .......... *A61K 39/0208* (2013.01); *A61K 39/39* (2013.01); *A61K 2039/552* (2013.01)

(58) Field of Classification Search
CPC ................................ A61K 39/00; A61K 39/02
USPC .................................. 24/9.1, 9.2, 93.1, 234.1
See application file for complete search history.

(56) References Cited

PUBLICATIONS

Gerlach C., et al. Coxiella burnetii immunogenic proeins as a basis for new Q fever diagnostic and vaccine development. Acta Virologica, 61:377-390, 2017.*
Xiong, X., et al. Exploratory study on Th1 epitope-induced protective immunity against Coxiella burnetii infection. PLOS, vol. 9, Iss. 1, e87206, pp. 1-9, 2014.*
Xiong et al., PLOS, vol. 9, Iss. 1, e877206, pp. 1-9, 2014.*
Gerlach et al., Acta viroiogica, 61:377-390, 2017.*

* cited by examiner

*Primary Examiner* — Rodney P Swartz
(74) *Attorney, Agent, or Firm* — Winstead PC

(57) ABSTRACT

A vaccine includes at least one bacterial antigen capable of producing an immune response in a host when the vaccine is administered at a dose that is sufficient for preventing or treating Q fever in the host. The vaccine composition confers immunity against Q fever without the reactogenic side effects observed in prior art vaccines.

7 Claims, 4 Drawing Sheets

VACCINE FOR IMMUNIZATION AGAINST Q-FEVER

CROSS-REFERENCES TO RELATED APPLICATIONS

This application claims the benefit of priority to and incorporates by reference the entire disclosure of U.S. Provisional Patent Application No. 62/550,625 filed on Aug. 28, 2017.

STATEMENT REGARDING FEDERALLY SPONSORED RESEARCH OR DEVELOPMENT

This invention was made with government support under Grant No. HDTRA-1-14-C-0113 awarded by the Department of Defense/Defense Threat Reduction Agency and Grant No. U54 AI057156 awarded by National Institutes of Health. The government has certain rights in the invention.

BACKGROUND

This section provides background information to facilitate a better understanding of the various aspects of the disclosure. It should be understood that the statements in this section of this document are to be read in this light, and not as admissions of prior art.

Coxiella burnetii infection of humans causes Q fever, a flu-like illness whose symptoms typically include fever, headache, and myalgia. In some cases, pneumonia and/or hepatitis can be present. Most patients resolve the infection and are immune to future C. burnetii infections. However, a minority of patients are unable to clear the bacteria and develop a chronic infection that most often presents as culture-negative endocarditis. C. burnetii is a Gram-negative bacterium that is typically transmitted by inhalation of aerosols that contain the bacteria. Once the organism is in the lungs, cells of the monocyte/macrophage lineage are infected. Infections can be initiated with small numbers of organisms, and the bacteria are slow growing in vivo. Humans therefore have a dose-dependent incubation period of 1 to 3 weeks before the onset of symptoms. At the time of symptom onset, C. burnetii organisms are often detectable in blood and serum.

Antibody responses develop 7 to 14 days after the onset of symptoms, with IgG antibody appearing shortly after IgM. Once IgG antibodies are present, C. burnetii quickly becomes undetectable in the blood. The mechanism by which C. burnetii is cleared from the blood is not known, but the timing correlates well with the development of immune responses. Although recent reports have suggested that C. burnetii DNA and antigen can be detected years after an acute infection, viable organisms are thought to be eliminated more quickly. However, the time required for complete clearance of viable C. burnetii in humans is not known. Cellular immune responses are thought to be initiated in humans with kinetics similar to those of the antibody response. However, this aspect has not been studied extensively.

Mouse models of Coxiella burnetii infection have been used to demonstrate that both CD4 and CD8 T cells are needed for clearance of the agent, with B cells playing a supporting role. Both serum and splenocytes from immune mice can transfer significant protection against C. burnetii to nave mice, but only transfer of immune splenocytes can confer protection on SCID mice. These studies have suggested that both T and B cell responses play a significant role in protective immunity in humans.

The only currently commercially available human vaccine against Q fever is Q-Vax®. Q-Vax® is a whole-cell formalin-inactivated preparation of the phase 1 Henzerling strain of C. burnetii. This vaccine is licensed for use only in Australia, where it is given primarily to farmers, abattoir workers, and laboratory personnel. The vaccine has been demonstrated to be highly effective and has a strong safety record. The vaccine cannot be given to persons already immune to C. burnetii, as this can cause a severe adverse reaction at the injection site. Because of this, potential vaccine recipients have to be carefully screened both for anti-Coxiella antibodies and by a skin test to identify potentially adverse responses. Both of these tests need to be negative before vaccination is advised.

The longevity of the protective immune response against C. burnetii provided by either natural infection or vaccination has not been well defined. The most common approach to evaluate immunity has been the measurement of the levels of serum antibody against C. burnetii. A study from the Netherlands that followed serology in a large group of naturally infected persons observed during that country's 2007-2011 Q fever epidemic found that IgG phase 2 serum antibody peaked at a mean of 53 days after symptom onset and then declined slowly, with the half-life of the antibody decay rate being 318 days. Thus, greater than 20% of acute Q fever patients could become seronegative 3 to 4 years after having the disease. Indeed, an analysis of Q fever patients in Australia 6 years after an outbreak found that 7/38 (18.4%) had become seronegative. A study of antibody responses in people vaccinated against Q fever found that only 60% had positive titers 20 months after vaccination, whereas 90% had detectable cellular immune responses. These results suggest that measurement of cellular immunity should be considered an indicator of previous exposure to C. burnetii. However, detection of cellular immunity in vaccinated subjects has also been reported as variable.

Due to the fact that that there is no commercially available human vaccine against Q fever available in the United States, coupled with the potential health risks that can arise with the administration of a whole cell preparation of C. burnetii, it would be advantageous to have a vaccine that showed efficacy in immunizing subjects against Q fever, while at the same time posing less of a health risk to the vaccine recipient. Embodiments of the invention described herein present a solution to this existing problem.

SUMMARY

This summary is provided to introduce a selection of concepts that are further described below in the detailed description. This summary is not intended to identify key or essential features of the claimed subject matter, nor is it intended to be used as an aid in limiting the scope of claimed subject matter.

An example of a multivalent antibacterial vaccine includes one or more heat-inactivated antigens, wherein at least one antigen produces an immune response in a host when said vaccine is administered at a dose that is sufficient for preventing Q fever in said host.

In some embodiments, the antigen is derived from Coxiella burnetii.

In some embodiments, the vaccine may be administered orally, intradermally, intranasally or intramuscularly.

In some embodiments, the molecular weight of the antigen is around 27 kDa.

In some embodiments, the vaccine further comprises one or more agents that enhance an immunogenic response.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of embodiments of the disclosure and do not limit the disclosure.

DESCRIPTION

Figure 1:
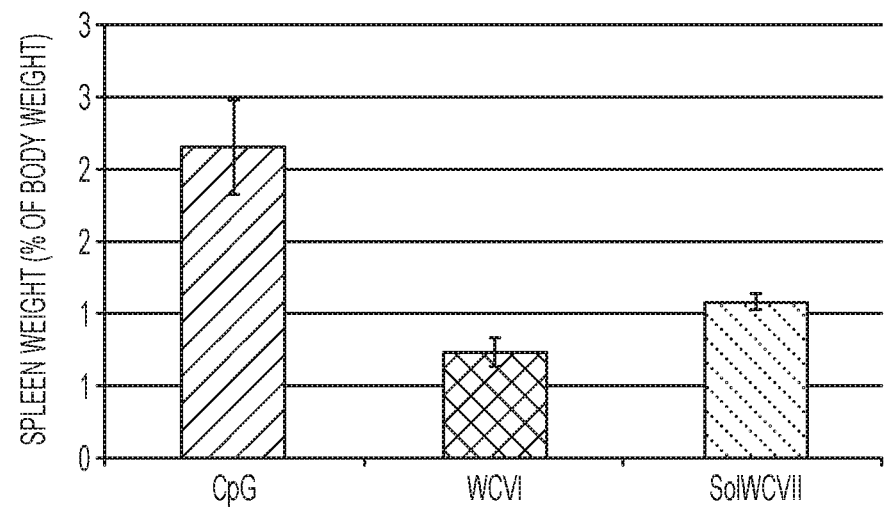
FIG. 1 is a graph of spleen weight as a percent of body weight in mice.

An embodiment of the invention is directed to a claimed vaccine composition comprising a solubilized bacterial extract, wherein the extract comprises at least one antigen that is capable of producing an immune response in a host, when said vaccine composition is administered at a dose that is sufficient for preventing the onset of Q fever in said host. In certain embodiments, the vaccine composition of claim 1, wherein the bacterial extract is derived from Coxiella burnetii. In other embodiments, the molecular weight of the antigen is between 25 kDa and 30 kDa. In further embodiments, the antigen has a molecular weight of around 27 kDa.

In certain embodiments, the vaccine composition further comprises one or more agents that enhance an immunogenic response when the composition is administered to a host. In some embodiments, the composition can be administered orally, intradermally, intranasally or intramuscularly.

The claimed invention relates to the production of a Q fever vaccine composition from either virulent or avirulent strains of Coxiella burnetii. A vaccine that provides significant, long-lasting protection against C. burnetii infection but does not induce reactogenic responses in previously sensitized subjects is provided. The claimed vaccine can be manufactured under BSL2 (Bio-Safety Level 2) laboratory conditions. In addition, the material has an improved safety profile in several animal models, compared with the only known commercial alternative, Q-Vax®, which is not approved for use in the US. The inventors of the present application have developed a vaccine compositon that provides comparable immunogenic protection against the disease caused by C. Burnetii, while eliminating reactogenic responses.

The Q-Vax® vaccine is produced from formalin inactivated purified C. Burnetii. Specifically, the vaccine contains whole cells of C. Burnetii. The Q-Vax® vaccine can only be produced in a BSAT (Biological Select Agents and Toxins) approved BSL3 (Bio-Safety Level 3) laboratory. As a result, production costs can be very high.

The claimed invention is directed to a vaccine composition that provides protection against Q fever to a subject to whom the vaccine is administered. The claimed vaccine composition is derived from solubilized proteins that are purified from C. burnetii cells. Bacterial cultures are grown in a selective growth media, following which the cells are lysed and soluble extracts of proteins are purified using standard protocols. The soluble extracts were further characterized to determine the composition of the protein antigens contained in the extracts. A protein having a molecular weight of between 25 kDa and 30 kDa was identified. Further characterization revealed that the molecular weight of the protein antigen was around 27 kDa.

The claimed vaccine does not contain whole cells like the Q-Vax® vaccine and therefore is safer for human use. Specifically, the claimed vaccine does not display many of the negative side effects of the Q-Vax® vaccine, such as, the occurrence of a severe adverse reaction at the injection site when the Q-Vax® vaccine is administered to persons who are already immune to C. burnetii. Therefore, the claimed vaccine can be safely administered without risk to individuals who have immunity to Q fever as a result of prior immunizations or due to having previously had the disease. This results in cost savings because the individuals do not need to be tested for the presence of anti-Coxiella antibodies or by a skin test prior to the administration of the claimed vaccine.

The ability to produce the claimed vaccine at a BSL2 laboratory rather than a BSAT-approved BSL3 facility, as required for the production of the Q-Vax® vaccine, provides a cheaper alternative for the commercial production of the claimed vaccine.

The claimed vaccine can be used to provide protection to military personnel entering parts of the world where the disease is endemic, as well as occupational health workers nationally and internationally (laboratory personnel, veterinarians, and farmers) who are at a high risk of exposure to this microorganism. Additionally, C. burnetii is listed as a tier 2 biothreat select agent by the CDC and the claimed vaccine could be used to protect civilian populations in the event of a bioterrorism attack.

The claimed vaccine composition generates significant, long-lasting immunity against exposure to C. burnetii. Experiments performed with the claimed vaccine show protection data in several small animal models that support the efficacy of this material compared to the Q-Vax® vaccine. Additionally, as further discussed below, the reactogenicity of the claimed vaccine composition does not result in any adverse effects, unlike the whole cell composition of the Q-Vax® vaccine.

Figure 2:
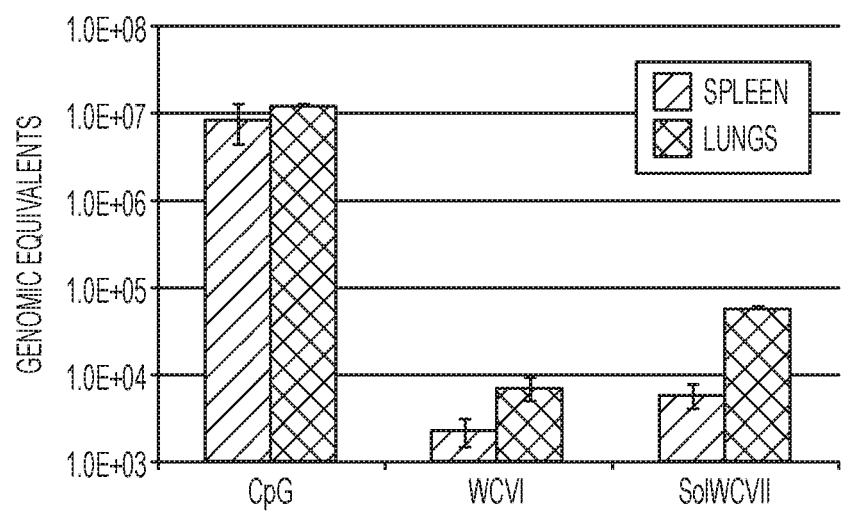
FIG. 2 is a graph of genomic equivalents (GE) of C. burnetii in spleen and lung tissue of mice.

FIGS. 1 and 2 demonstrate protection from Q fever in mice by WCVI (a prior art vaccine) and SolWCVII (vaccine composition of the invention). Mice were vaccinated using a control (CpG, no vaccine), WCVI, or SolWCVII. Following a seven week rest, the vaccinated mice were challenged with C. burnetii through aerosol administration. Following a fourteen day infection period, the mice were sacrificed and the weight of the spleens was measured as a function of total body weight. Splenomegaly, i.e., an enlarged spleen, is a well-defined correlate of Q fever disease. As shown in FIG. 1, the weight of the spleens, as a function of total body weight, obtained from mice that were vaccinated with WCVI or SolWCVII were comparable to each other, and far lower than the weight of the spleens obtained from the control mice, i.e., which had not received any vaccine. The results indicate that the vaccine composition of the claimed invention shows protective benefits against disease caused by *C. burnetii* that is comparable to a prior art vaccine having known beneficial effects in preventing the onset of Q fever.

Genomic Equivalents (GE) is a quantitative PCR-based method for detecting the number of bacteria present within a tissue. As shown in FIG. 2, the amount of *C. burnetii* found in the lung and spleen tissues of mice that were vaccinated with WCVI or SolWCVII were comparable to one another, and far lower than the amounts found in the control mice that did not receive any vaccine. These results further demonstrate that the vaccine composition of the claimed invention shows protective benefits against disease caused by *C. burnetii*.

Figure 3:
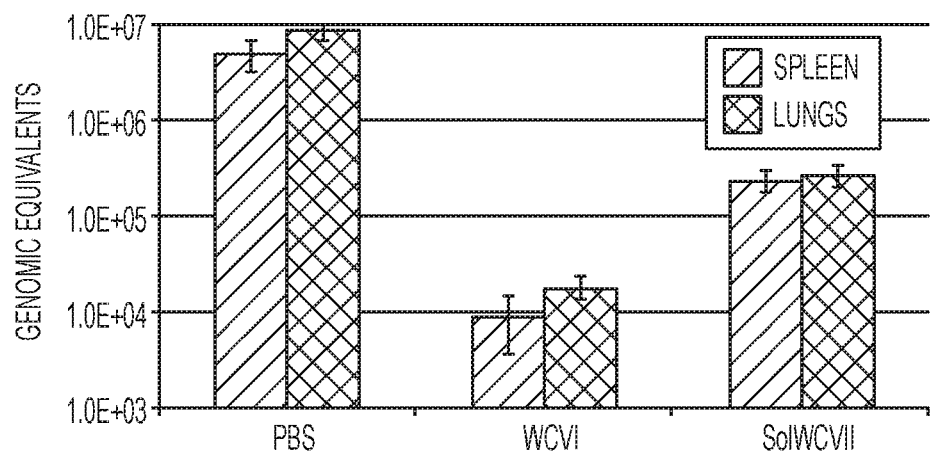
FIG. 3 is a graph of genomic equivalents (GE) of C. burnetii in spleen and lung tissue of guinea pigs.
Figure 4:
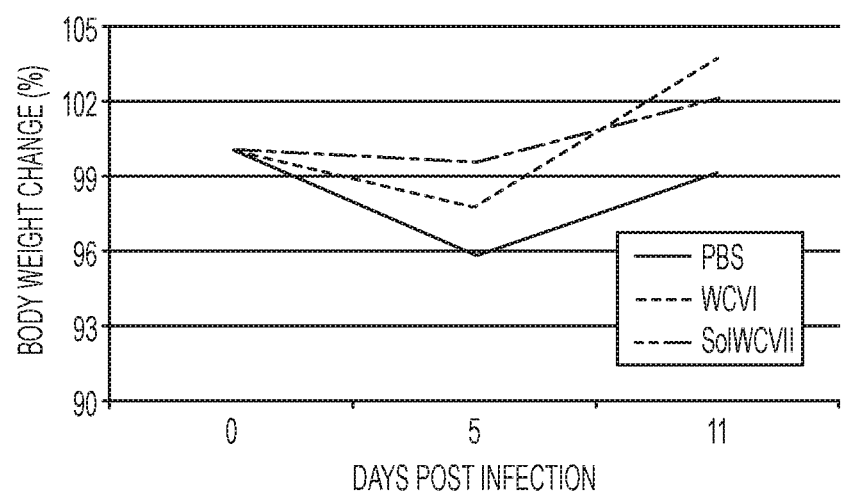
FIG. 4 is a graph of body weight change versus days post infection in guinea pigs.
Figure 5:
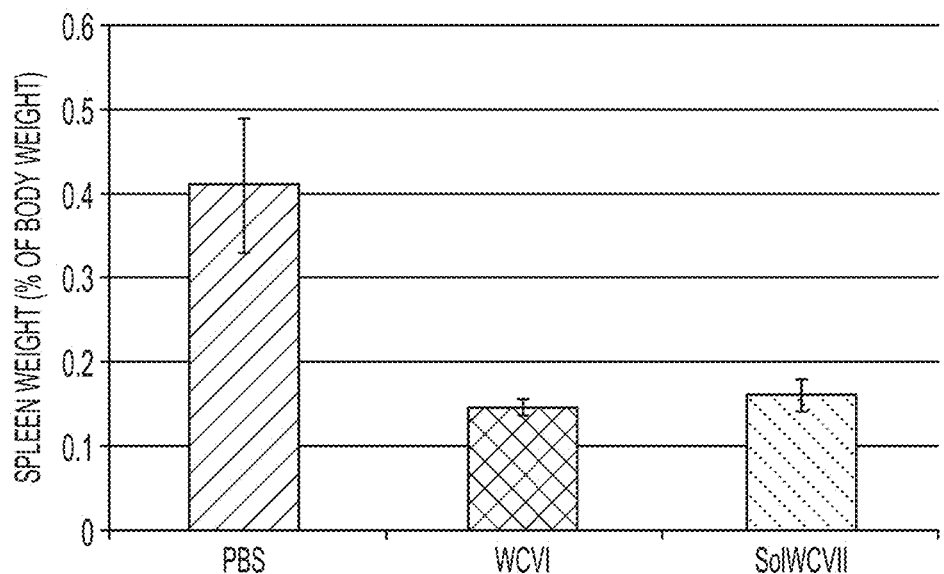
FIG. 5 is a graph of spleen weight as a percent of body weight in guinea pigs.

FIG. 3, FIG. 4 and FIG. 5 demonstrate protection from Q fever in guinea pigs by WCVI and SolWCVII. Guinea pigs were vaccinated using a control (PBS, no vaccine), WCVI, or SolWCVII. Following a seven week rest, the vaccinated guinea pigs were challenged with *C. burnetii*. Following a fourteen day infection period, the guinea pigs were sacrificed and the weight of the spleens was measured as a function of total body weight.

As shown in FIG. 3, the amount of *C. burnetii* found in the lung and spleen tissues of guinea pigs that were vaccinated with WCVI or SolWCVII were comparable to one another, and far lower than the amounts found in the control guinea pigs that did not receive any vaccine. These results further demonstrate that the vaccine composition of the claimed invention shows protective benefits against disease caused by *C. burnetii*.

FIG. 4 shows that guinea pigs that were vaccinated with SolWCVII underwent smaller changes in body weight in the first eleven days post infection compared to those vaccinated with WCVI. Since the change in body weight can be directly attributed to the enlargement of the spleen of the infected animals, the results in FIG. 4 indicate that SolWCVII conferred greater immunity to the onset of disease in the test subjects than WCVI.

FIG. 5 shows that the weight of the spleens, as a function of total body weight, obtained from guinea pigs that were vaccinated with WCVI or SolWCVII were comparable to each other, and far lower than the weight of the spleens obtained from the control guinea pigs, i.e., which had not received any vaccine. Therefore, the administration of the vaccines to the guinea pigs conferred protection from disease as illustrated by the absence of splenomegaly relative to the control guinea pigs that received neither vaccine.

Figure 6:
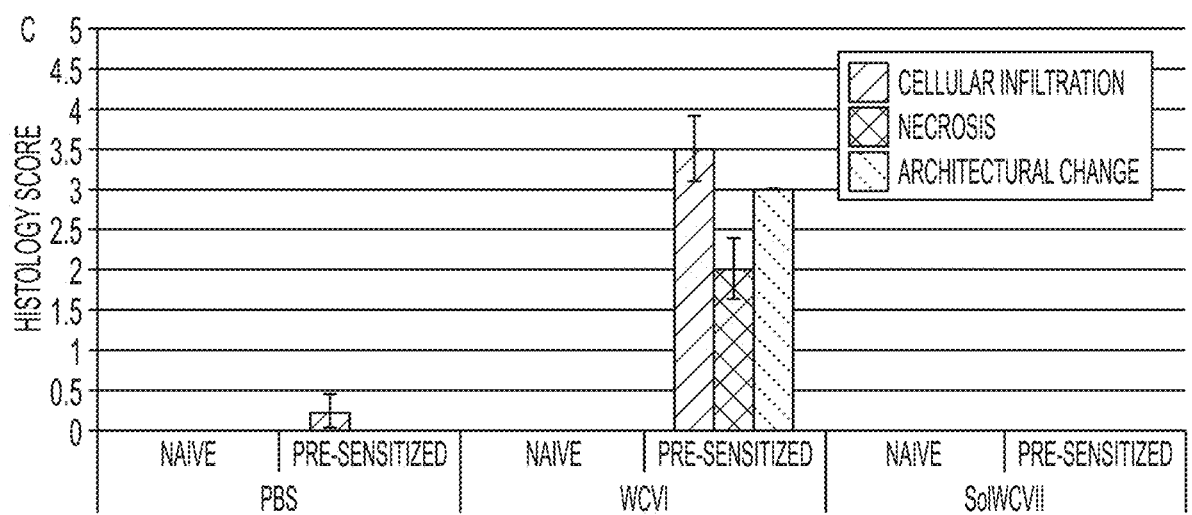
FIG. 6 shows the results of reactogenicity testing in guinea pigs.

FIG. 6 shows the results of reactogenicity testing in guinea pigs. Guinea pigs were challenged with a dose of *C. Burnetii* via aerosol administration. This process was performed to pre-sensitize the guinea pigs prior to vaccine administration. The guinea pigs developed an infection as determined by episodes of fever. The fever resolved after 14 days, following which the guinea pigs were rested for an additional five (5) weeks. Following the period of rest, the guinea pigs were vaccinated with PBS (control), or 30 µg of WCVI or SolWCVII. Necroscopy was performed after 14 days. As shown in FIG. 6, the vaccination sites of guinea pigs vaccinated with the PBS control showed a small amount of cellular infiltration, but did not show measurable necrosis or architectural change. The guinea pigs vaccinated with WCVI showed significant cellular infiltration, necrosis and architectural change compared with the controls. The subjects vaccinated with SolWCVII exhibited no significant necrosis or inflammation at the injection site compared to vaccination sites of guinea pigs vaccinated with WCVI. This result shows that SolWCVII can safely be used to immunize subjects having immunity to *C. burnetii* as a result of having previously contracted Q fever, whereas the prior art vaccine causes a significant adverse reaction at the injection site of a subject having immunity to *C. burnetii*.

Rhesus macaque monkeys were vaccinated with WCVI. Following a four (4) week rest period, the subjects were vaccinated with PBS (control), WCVI and SolWCVII. Induration and erythema at the injection site was monitored for 14 days and scored by a pathologist.

Figure 7:
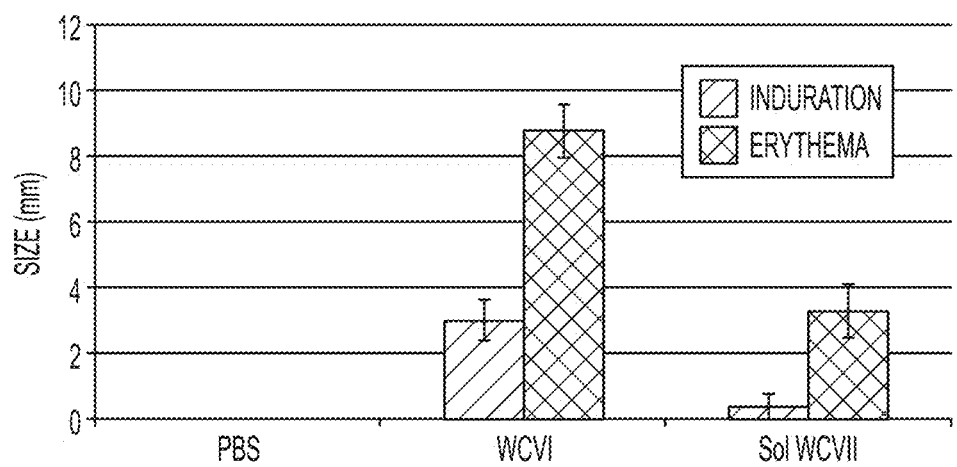
FIG. 7 shows the results of reactogenicity testing in monkeys.

FIG. 7 shows that monkeys that were vaccinated with SolWCVII exhibited less induration or erythema at the injection site compared to Rhesus macaques vaccinated with WCVI. This result shows that SolWCVII can safely be used to immunize subjects having immunity to *C. burnetii* as a result of having been immunized with the prior art vaccine, whereas the second administration of the prior art vaccine caused a significant adverse reaction at the injection site of a subject that had been previously vaccinated with the prior art vaccine.

While this invention has been particularly shown and described with references to example embodiments thereof, it will be understood by those skilled in the art that various changes in form and details may be made therein without departing from the scope of the invention encompassed by the appended claims. Conditional language used herein such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. While the above detailed description has shown, described, and pointed out novel features as applied to various embodiments, it will be understood that various omissions, substitutions, and changes in the form and details of the devices illustrated can be made without departing from the spirit of the disclosure. As will be recognized, the processes described herein can be embodied within a form that does not provide all of the features and benefits set forth herein, as some features can be used or practiced separately from others. The scope of protection is defined by the appended claims rather than by the foregoing description. All changes which come within the meaning and range of equivalency of the claims are to be embraced within their scope.

What is claimed is:

1. A vaccine composition comprising a bacterial extract purified from *Coxiella burnetti* cells, wherein the bacterial extract comprises a protein antigen that is capable of producing an immune response in a host, when said vaccine composition is administered at a dose that is sufficient for preventing onset of Q fever in said host, and wherein the protein antigen is SolWCVII.

2. The vaccine composition of claim 1, wherein the molecular weight of the protein antigen is at least 27 kDa.

3. The vaccine composition of claim 1, wherein the composition further comprises one or more agents that enhance an immunogenic response.

4. The vaccine composition of claim 1, wherein the composition prevents splenomegaly when the host is exposed to *Coxiella burnetii*.

5. The vaccine composition of claim 1, wherein the composition prevents reactogenicity at an injection site even when the host possesses immunity to infection by *Coxiella burnetii*.

6. The vaccine composition of claim 1, wherein the *Coxiella burnetii* is a virulent strain.

7. The vaccine composition of claim 1, wherein the *Coxiella burnetii* is an avirulent strain.

* * * * *